United States Patent
Lehay et al.

(10) Patent No.: US 10,456,358 B2
(45) Date of Patent: Oct. 29, 2019

(54) ISOXAZOLINE COMPOSITIONS AND USE THEREOF IN THE PREVENTION OR TREATMENT OF PARASITE INFESTATIONS IN ANIMALS

(71) Applicant: Intervet Inc., Madison, NJ (US)

(72) Inventors: Anne Lehay, Angers (FR); Annie Flochlay-Sigognault, Madison, NJ (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/102,414

(22) PCT Filed: Dec. 19, 2014

(86) PCT No.: PCT/EP2014/078634
§ 371 (c)(1),
(2) Date: Jun. 7, 2016

(87) PCT Pub. No.: WO2015/091898
PCT Pub. Date: Jun. 25, 2015

(65) Prior Publication Data
US 2016/0317439 A1 Nov. 3, 2016

(30) Foreign Application Priority Data

Dec. 20, 2013 (EP) .................................... 13199006

(51) Int. Cl.
| | | |
|---|---|---|
| A61K 31/42 | (2006.01) | |
| A61K 9/00 | (2006.01) | |
| A61K 47/10 | (2017.01) | |
| A61K 47/14 | (2017.01) | |
| A61K 47/22 | (2006.01) | |
| A61K 47/26 | (2006.01) | |
| A23K 20/132 | (2016.01) | |
| A23K 50/75 | (2016.01) | |
| A23K 50/30 | (2016.01) | |
| A23K 20/137 | (2016.01) | |
| A23K 20/105 | (2016.01) | |
| A01N 43/80 | (2006.01) | |
| A01N 25/02 | (2006.01) | |

(52) U.S. Cl.
CPC ............ *A61K 9/0095* (2013.01); *A01N 25/02* (2013.01); *A01N 43/80* (2013.01); *A23K 20/105* (2016.05); *A23K 20/132* (2016.05); *A23K 20/137* (2016.05); *A23K 50/30* (2016.05); *A23K 50/75* (2016.05); *A61K 31/42* (2013.01); *A61K 47/10* (2013.01); *A61K 47/14* (2013.01); *A61K 47/22* (2013.01); *A61K 47/26* (2013.01)

(58) Field of Classification Search
CPC ........ A61K 31/42; A61K 47/10; A61K 47/14; A61K 47/22; A61K 47/26; A61K 9/0095; A01N 25/02; A01N 43/80; A23K 20/105; A23K 20/132; A23K 20/137; A23K 50/30; A23K 50/75
See application file for complete search history.

(56) References Cited

U.S. PATENT DOCUMENTS

| | | | |
|---|---|---|---|
| 7,662,972 | B2 | 2/2010 | Mita et al. |
| 2007/0066617 | A1 | 3/2007 | Mita et al. |
| 2010/0125097 | A1* | 5/2010 | Soll ........................ A01N 43/56 |
| | | | 514/407 |
| 2013/0065846 | A1 | 3/2013 | Soli et al. |
| 2013/0095126 | A1 | 4/2013 | Perret |

FOREIGN PATENT DOCUMENTS

| | | |
|---|---|---|
| EP | 1731512 A1 | 12/2006 |
| EP | 2308857 A1 | 4/2011 |
| EP | 2545777 A1 | 4/2014 |
| WO | 2005/085216 | 9/2005 |
| WO | 2007/079162 A1 | 7/2007 |
| WO | 2007075459 A2 | 7/2007 |
| WO | 2007/053902 A1 | 6/2008 |
| WO | 2009/002809 A2 | 12/2008 |
| WO | 2009/024541 | 2/2009 |
| WO | 2009/080250 A2 | 7/2009 |
| WO | 2010/070068 A2 | 6/2010 |
| WO | 2010/079077 A1 | 7/2010 |
| WO | 2011154434 A2 | 12/2011 |
| WO | 2012/089622 A2 | 5/2012 |
| WO | 2012/089623 A1 | 5/2012 |
| WO | 2012107533 A1 | 8/2012 |
| WO | 2013026695 A1 | 2/2013 |
| WO | 2013026931 A1 | 2/2013 |
| WO | 2013039948 A1 | 3/2013 |
| WO | 2013050302 A1 | 4/2013 |
| WO | 2009/003075 A1 | 6/2015 |

OTHER PUBLICATIONS

International Search Report for PCTEP/2014/078634 dated Feb. 6, 2015.
Hinkle, NC et al., Efficacy and safety assessment of a water-soluble formulation of fluralaner for treatment of natural ornithonyssus sylviarum infestations in laying hens, Parasites & Vectors, 2018, pp. 1-6, 11(99).
Sparagano Oae et al., Significance and control of the poultry red mite, *Dermanyssus gallinae*, Annu. Rev. Entomol, 2014, pp. 447-466, 59.
Thomas E et al., Field efficacy and safety of fluralaner solution for administration in drinking water for the treatment of poultry red mite (*Dermanyssus gallinae*) intestations in commercial flocks in Europe, Parasites & Vectors, 2017, pp. 1-9, 10(457).

(Continued)

*Primary Examiner* — Sarah Pihonak

(57) ABSTRACT

This invention is directed to a pharmaceutical composition for drinking water administration comprising isoxazoline compounds of formula (I) and a polysorbate surfactant and diethylene glycol monoethyl ether (transcutol); and the use of the composition to treat or prevent parasite infestations of animals.

11 Claims, No Drawings

(56) References Cited

OTHER PUBLICATIONS

Belikov, Relationship Between Molecular Structure of Substances and Their Effect on an Organism, Pharmaceutical chemistry, 1993, pp. 43-47, RU.

* cited by examiner

ISOXAZOLINE COMPOSITIONS AND USE THEREOF IN THE PREVENTION OR TREATMENT OF PARASITE INFESTATIONS IN ANIMALS

CROSS-REFERENCE TO RELATED APPLICATIONS

This application is a national stage entry under 35 U.S.C. § 371 of PCT/EP2014/078634, filed on Dec. 19, 2014, which claims priority EP Application No. 13199006.1, filed on Dec. 20, 2013. The content of PCT/EP2014/078634 is hereby incorporated by reference in its entirety.

FIELD OF INVENTION

The invention is in the field of pharmaceutical compositions comprising isoxazoline compounds for use in animals.

BACKGROUND OF INVENTION

Isoxazoline compounds are known in the art and compounds from this class are known to possess excellent activity against parasite infestations of animals.

Isoxazoline compounds and their use as antiparasitics are e.g. described in US patent application US 2007/0066617, and International Patent applications WO 2005/085216, WO 2007/079162, WO 2009/002809, WO 2009/024541, WO 2009/003075, WO 2010/070068 and WO 2010/079077.

Although different administration routes are known, the administration of active ingredients via drinking water systems to intensively reared animals such as pigs and poultry is beneficial, because it enables the simultaneous administration to a high number of animals during a defined time period.

Many pig and poultry farms are already equipped with the necessary devices to administer medication via drinking water systems.

Such drinking water systems on farms are complex systems of tanks, dosing pumps, pipes, coils, pen drinkers and nipples. An average stable may contain hundreds of meters of pipes with many coils and hundreds of individual cups and/or nipples.

The water in the drinking water system in a pig or poultry house obeys the principles of laminar flow through the pipes and coils and is subjected to the so called "shearing" forces which will affect the rate of flow. In such complex piping system there are considerable risks for segregation or sedimentation of the medication, certainly when it concerns water insoluble compounds.

The effectiveness of medication via the drinking water system in general largely depends on the quality of the composition (and its stability in the drinking water system) and the palatability of the medication.

A suitable composition should provide maximum availability of the active ingredient, minimal or no segregation and sedimentation of the active compound in the drinking water system, medication pumps, nipples cups etc., a precise dosing and homogeneous distribution of the active ingredient in the drinking water and a guaranteed stability of the active ingredient in the composition itself and after dilution to the target concentration in the medicated drinking water.

Such pharmaceutical compositions are not available in the prior art.

The pharmaceutical composition that was provided in the current invention addresses these requirements.

SUMMARY OF THE INVENTION

The current invention provides the use of a pharmaceutical composition comprising an isoxazoline compound of formula (I),

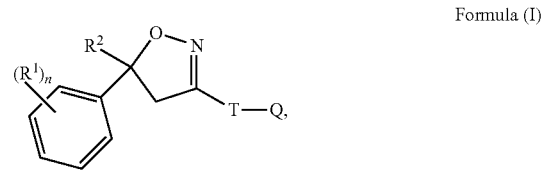

Formula (I)

Wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5- or 6-membered ring, which is optionally substituted by one or more radicals Y, Y=methyl, halomethyl, halogen, CN, $NO_2$, $NH_2$—C=S, or two adjacent radicals Y form together a chain, especially a three or four membered chain;

Q=X—$NR^3R^4$ or a 5-membered N-heteroaryl ring, which is optionally substituted by one or more radicals;

X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

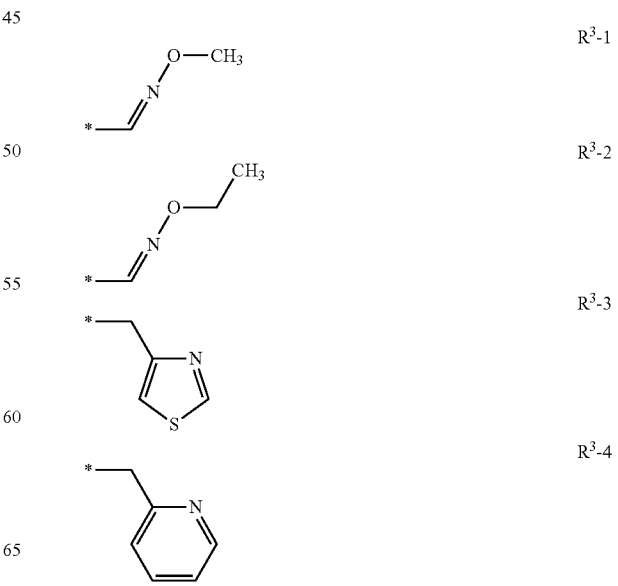

R³-5 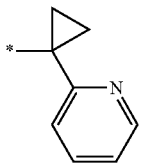

R³-6 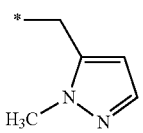

R³-7 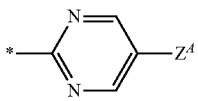

R³-8 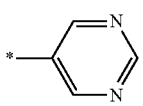

R³-9 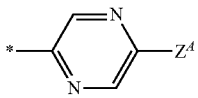

R³-10 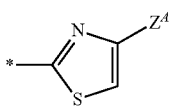

R³-11 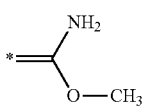

R³-12 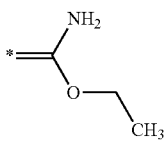

R³-13 

R³-14 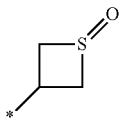

R³-15 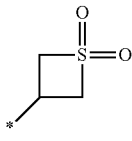

wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

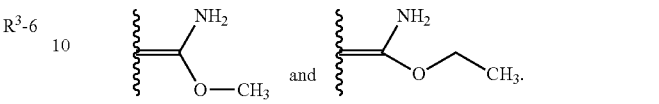

or a salt or solvate thereof, and a pharmaceutically acceptable carrier comprising diethylene glycol monoethyl ether and a polysorbate surfactant for the manufacture of a medicament for drinking water administration for the prevention or treatment of parasite infestations of animals.

Another aspect of the current invention is medicated drinking water comprising a pharmaceutical composition as described above and water.

Another aspect of the current invention is a method of preparing medicated drinking water for animals by diluting a pharmaceutical composition as described above with drinking water.

Another aspect of the current invention is medicated drinking water as described above for use in treating or preventing parasite infestations of animals.

DEAILED DESCRIPTION OF THE INVENTION

It has been shown by the inventors that pharmaceutical compositions according to the invention, that comprises an isoxazoline compound as described below, and a pharmaceutically acceptable carrier comprising diethylene glycol monoethyl ether and a polysorbate surfactant are stable and effective in the prophylaxis (prevention) and therapy (treatment) of parasitic infestations of animals.

It has been further shown that such compositions are suitable to prepare medicated water that is stable enough and can be distributed homogeneously in the system to allow administration of an effective amount of isoxazoline compounds to animals through drinking water systems.

The isoxazoline compound for use in the current invention can be described by Formula (I):

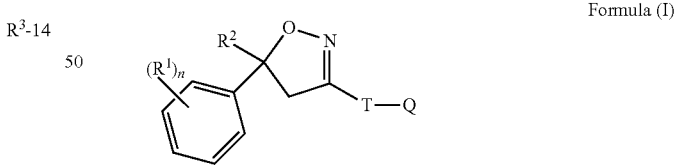

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C═S, or two adjacent radicals Y form together a chain CH═CH—CH═CH, N═CH—CH═CH, CH═N—CH═CH, CH—CH═N—CH, or CH═CH—CH═N, HC═HC—CH, CH—CH═CH, CH═CH—N, N—CH═CH;

Q=X—NR³R⁴ or a 5-membered N-heteroaryl ring, which is optionally substituted by one or more radicals $Z^A$, $Z^B Z^D$;

X=CH₂, CH(CH₃), CH(CN), CO, CS,

R³=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

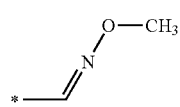
R³-1

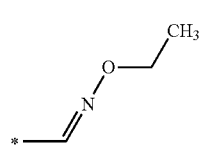
R³-2

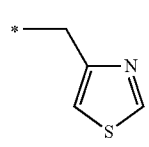
R³-3

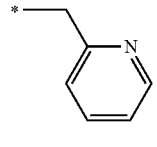
R³-4

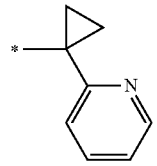
R³-5

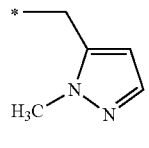
R³-6

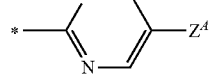
R³-7

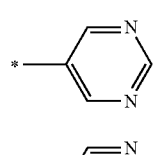
R³-8

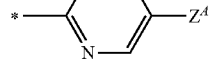
R³-9

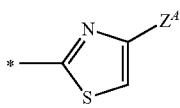
R³-10

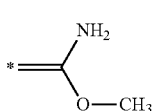
R³-11

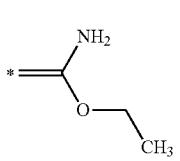
R³-12

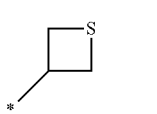
R³-13

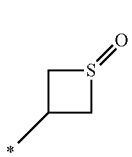
R³-14

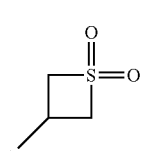
R³-15

R⁴=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or R³ and R⁴ together form a substituent selected from the group consisting of:

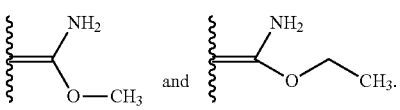

wherein $Z^A$=hydrogen, halogen, cyano, halomethyl (CF₃).

In one preferred embodiment in Formula (I) T is selected from

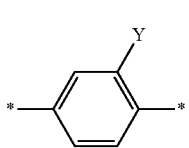
T-1

-continued
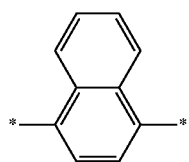
T-2
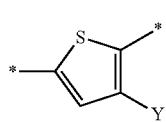
T-3
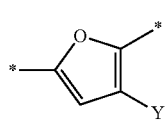
T-4
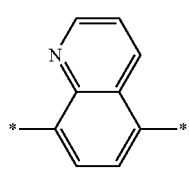
T-5
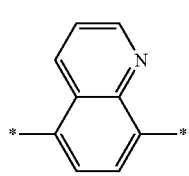
T-6
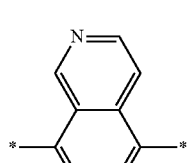
T-7
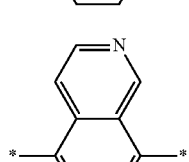
T-8
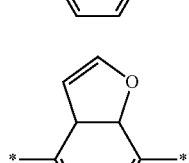
T-9
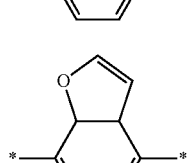
T-10
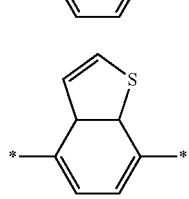
T-11
-continued
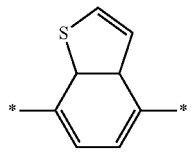
T-12
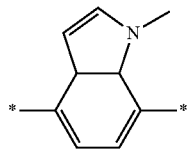
T-13
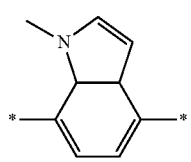
T-14
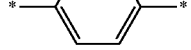
T-15
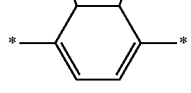
T-16
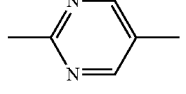
T-17
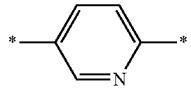
T-18
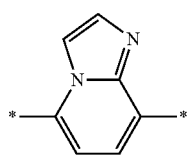
T-19
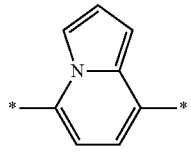
T-20
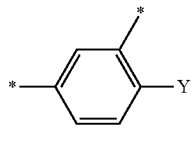
T-21
T-22 wherein in T-1, T-3 and T-4 the radical Y is hydrogen, halogen, methyl, halomethyl, ethyl, haloethyl.
In an preferred embodiment in Formula (I) Q is selected from
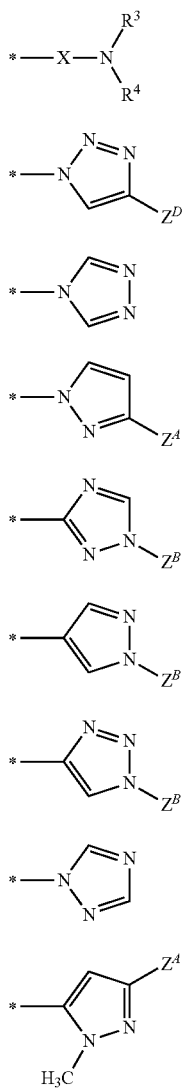
wherein $R^3$, $R^4$, X and $Z^A$ are as defined above.
$Z^B =$
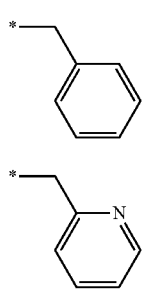
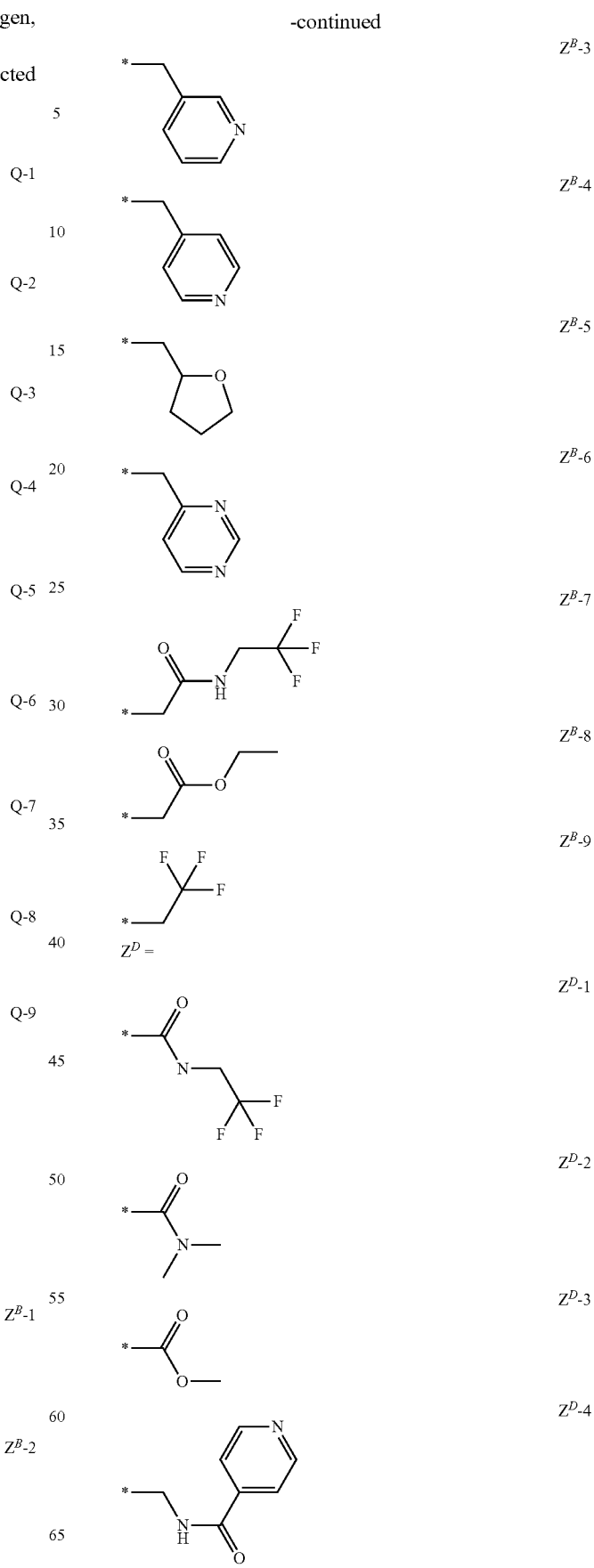

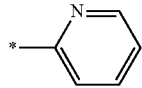

$Z^D$-5

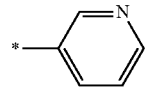

$Z^D$-6

Preferred isoxazoline compounds of Formula (I) for use in the current invention are:

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CH_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | | T-2 | — | Q-7 | $Z^B$-7 | |
| 3-Cl, 5Cl | $CF_3$ | — | | T-2 | — | Q-5 | $Z^B$-7 | |
| 3-Cl, 5Cl | $CF_3$ | — | | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-Cl, 5Cl | $CF_3$ | $CH_2C(O)NHCH_2CH_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CH_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CH_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CH_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-Cl, 5-Cl | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CH_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-$CF_3$, 5-$CF_3$ | $CF_3$ | $CH_2C(O)NHCH_2CH_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CH_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $CH_2C(O)NHCH_2CH_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

Especially preferred isoxazoline compounds for use in the current invention are

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | | T-2 | — | Q-7 | $Z^B$-7 | |

-continued

| (R¹)ₙ | R² | R³ | R⁴ | T | Y | Q | Z | X |
|---|---|---|---|---|---|---|---|---|
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred isoxazoline compound for use in the current invention has the Formula (II),

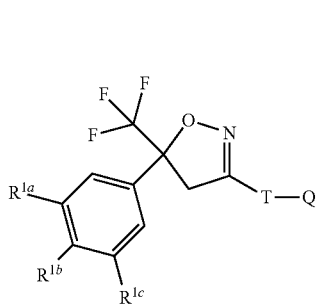

Formula II wherein $R^{1a}$, $R^{1b}$, $R^{1c}$ are independently from each other hydrogen, Cl or CF₃, preferably $R^{1a}$ and $R^{1c}$ are Cl or CF₃ and $R^{1b}$ is hydrogen, T is

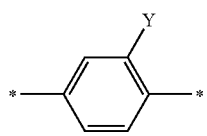

T-1

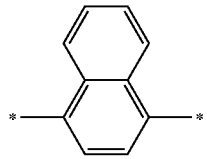

T-2

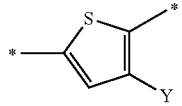

T-3

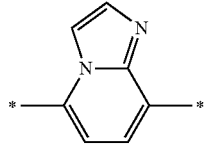

T-20

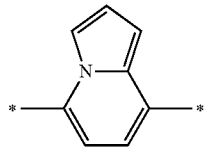

T-21 wherein

Y is methyl, bromine, Cl, F, CN or C(S)NH₂, and

Q is as described above.

In another preferred embodiment in Formula (II) R³ is H and R⁴ is —CH₂—C(O)—NH—CH₂—CF₃, —CH₂—C(O)—NH—CH₂—CH₃, —CH₂—CH₂—CF₃ or —CH₂—CF₃.

In a preferred embodiment the isoxazoline compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3 -USAN fluralaner).

In another embodiment the isoxazoline compound is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the isoxazoline compound is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another preferred embodiment the isoxazoline compound is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162-.

In another embodiment the isoxazoline compound is Ethanone, 1-[5'-[(5S)-5-(3,5-dichloro-4-fluorophenyl)-4,5-dihydro-5-(trifluoromethyl)-3-isoxazolyl]spiro[azetidine-3,1'(3'H)-isobenzofuran]-1-yl]-2-(methylsulfonyl)-(Sarolaner) (CAS RN-1398609-39-6).

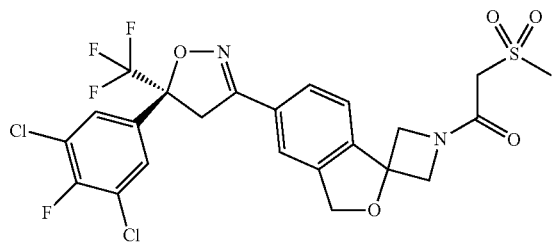 [SMILES: CS(=O)(=O)CC(=O)N1CC2(C1)OCc1cc(C3=NO[C@@](c4cc(Cl)c(F)c(Cl)c4)(C(F)(F)F)C3)ccc12]

In another embodiment the isoxazoline compound is 2-Thiophenecarboxamide, 5-((5S)-4,5-dihydro-5-(3,4,5-trichlorophenyl)-5-(trifluoromethyl)-3-isoxazolyl)-3-methyl-N-(2-oxo-2-((2,2,2-trifluoroethyl)amino)ethyl)- (INN Lotilaner) (CAS RN-1369852-71-0).

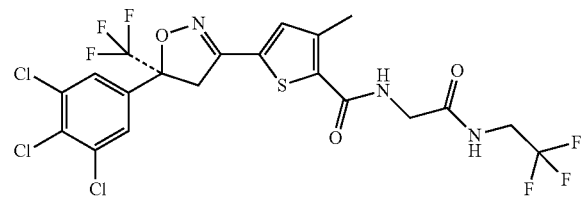

In another embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

The method (or use) of this invention comprises to use racemic mixtures, for example, equal amounts of the enantiomers of such isoxazoline compounds as described above. In addition, the method of this invention includes isoxazoline compounds that are enriched compared to the racemic mixture in an enantiomer of Formula 1. Also included are the essentially pure enantiomers of such isoxazoline compounds.

When enantiomerically enriched, one enantiomer is present in greater amounts than the other, and the extent of enrichment can be defined by an expression of enantiomeric excess ("ee"), which is defined as (2x-I)·100%, where x is the mole fraction of the dominant enantiomer in the mixture (e.g., an ee of 20% corresponds to a 60:40 ratio of enantiomers). Preferably the compositions for use in the current invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Isoxazoline compounds as described above can comprise additional chiral centers. The method of this invention comprises racemic mixtures as well as enriched and essentially pure stereo configurations at these additional chiral centers.

The reference to isoxazoline compound in this specification includes enantiomers, salts and solvates as well as N-oxides thereof that can be produced by conventional methods.

The isoxazoline compound as disclosed above is generally present in the composition of the current invention in an amount of about 0.001 mg/ml to about 100 mg/ml.

A preferred pharmaceutical composition according to the current invention is a concentrated solution. Such concentrated solution comprises between 1.5 mg/ml and 100 mg/ml of the isoxazoline compound, especially fluralaner.

Compositions according to the invention have especially favorable properties, such as extended stability after storage and lack of precipitation of the isoxazoline compound after dilution of such composition in water.

The pharmaceutical composition of the current invention comprises a pharmaceutically acceptable carrier comprising diethylene glycol monoethyl ether and a polysorbate surfactant.

Such carrier must be substantially pharmaceutically or veterinary pure and its components must be non-toxic in the amounts employed and must be compatible with the isoxazoline compounds.

Diethyleneglycol monoethyl ether is used as a solvent in such a carrier. Diethyleneglycol monoethyl ether or transcutol (CAS no. 31692-85-0) is the compound of formula (III), $$R_1—[O—(CH_2)_2]_x—OR_2 \quad \text{Formula (III)}$$

wherein $R_1=C_2H_5$, $R_2=H$ and $x=2$.

Products that contain diethyleneglycol monoethyl ether are e.g. those known and commercially available, e.g. under the trade name Transcutol® from Gattefosse, (St Priest, France), in particular the products Transcutol® V, P and HP.

Synonym names for diethyleneglycol monoethyl ether or transcutol are: 1-Hydroxy-3,6-dioxaoctane, 2-(2'-Ethoxyethoxy) ethanol, 2-(2-Ethoxyethoxy) ethanol, 2-(2-Ethoxyethyoxy) ethanol, 3,6-Dioxa-1-octanol, 3,6-Dioxa-1-oktanol, 3,6-Dioxaoctan-1-ol, Aethyldiaethylenglycol, APV, Carbitol, Carbitol cellosolve, Carbitol solvent, DEGEE, DEGMEE, Diethylene glycol ethyl ether, Diethylene glycol monoethyl ether, Diglycol monoethyl ether, Dioxitol, Dowanol, Dowanol 17, Dowanol DE, Ektasolve DE, Ethanol, 2,2'-oxybis-, monoethyl ether, Ethanol, 2-(2-ethoxyethoxy)-, Ether monoethylique du diethylene glycol, Ethoxy diglycol, Ethoxydiglycol, Ethyl carbitol, Ethyl diethylene glycol, Ethyl digol, Ethyldiethylene glycol, Ethyl carbitol.

The diethyleneglycol monoethyl ether is generally present in the composition of the invention in an amount of about 10% to about 75% by weight of the carrier.

In some embodiments, the diethyleneglycol monoethyl ether is present from about 15% to about 60% by weight, from about 20% to about 55%, or from about 25% to about 50% by weight or about 12.5%, 25% or 37.5% by weight of the carrier.

In one embodiment the composition comprises at least one additional solvent.

In one embodiment the composition additionally comprises ethyl lactate. Ethyl lactate, also known as lactic acid ethyl ester, is a monobasic ester formed from lactic acid and ethanol.

In some embodiments, the ethyl lactate is present from about 10% to about 50% by weight, or from about 10% to about 40% by weight or about 12.5%, 25% or 37.5% of the carrier.

Preferably the ratio of diethyleneglycol monoethyl ether to the additional solvent, such as ethyl lactate is around 75%/25% w/w.

In one embodiment such additional solvent is a pyrrolidone solvent such as 2 pyrrol.

In some embodiments, the 2 pyrrol is present from about 10% to about 30% by weight, or about 12.5% or 25% by weight of the carrier.

Polysorbate surfactants have shown favorable characteristics in the composition according to the current invention. In general one or a combination of more than one polysorbate surfactants can be present.

In contact with water the polysorbate surfactant creates micelles around the isoxazoline compound that is solubilized in diethyleneglycol monoethyl ether and maintains the solubilized isoxazoline compound in an aqueous environment.

A polysorbate surfactant (Sorbitan ester, poly(oxy-1,2 ethanediyl) derive, Tween) is a water soluble nonionic surface-active agent comprised of complex esters and esterethers derived from hexahydric alcohols, alkylene oxides and fatty acids by adding polyoxyethylene chains to hydroxyl of sorbitol and hexitrol anhydrides (hexitans and hexides) derived from sorbitol and then partially esterifying with the common fatty acids such as lauric, palmitic, stearic and oleic acids.

In one embodiment the polysorbate surfactant is selected from one or more of Tween 20, Tween 40, Tween 60 and Tween 80, also known in the pharmaceutical industry as polysorbate 20, polysorbate 40, polysorbate 60 and polysorbate 80. Polysorbate 20 (Polyoxyethylated Sorbitan Monolaurate,) is a laurate ester, Polysorbate 60 (Polyoxyethylated Sorbitan Monostearate) is a mixture of stearate and palmitate esters; and Polysorbate 80 (Polyoxyethylated Sorbitan Monooleate) is an oleate ester.

Such polysorbate surfactants are commercially available and/or can be prepared by techniques known in the art.

In one preferred embodiment the polysorbate surfactant is polysorbate 80 (polyoxyethylene sorbitan monoleate, Tween 80) having the chemical name polyoxyethylene (20) sorbitan monooleate, e.g. available from ICI Specialty Chemicals.

The polysorbate surfactant is present in the composition from about 5% to about 89% by weight of the carrier.

In some embodiments, the concentration of the polysorbate surfactant is from about 30% to about 80% by weight, from about 50% to about 75% by weight, or about 75% by weight of the carrier.

The ratio of diethylene glycol monoethyl ether to polysorbate surfactant is <50:50% w/w, preferably 15/85, 20/80, 25/75, 30/70, 35/65. 40/60% w/w. In one embodiment the ratio is preferably about 25/75% w/w. This has been shown to result in especially stable pharmaceutical compositions.

In addition the carrier may comprise other non-active ingredients or excipients that are known to the skilled person e.g. as described in "Gennaro, Remington: The Science and Practice of Pharmacy" (20th Edition, 2000) incorporated by reference herein.

Optionally, the pharmaceutical composition may also contain an antifoaming agent, such as for example, simethicone emulsion 30% USP, sodium oleate, sodium caprylate or mixtures thereof.

The antifoaming agent is present in sufficient concentration to prevent foam formation when the composition of the instant invention is diluted with water. The simethicone emulsion may be present at concentration of from about 0.001% by weight to about 0.005% by weight of the carrier.

Optionally, the pharmaceutical composition may also contain a preservative. The preservative is one known to those skilled in the art, and can be e.g. benzyl alcohol, butylparaben sodium salt, methylparaben sodium salt, propylparaben sodium salt and mixtures thereof. It is generally present in an amount of from about 0.01% to about 3% by weight of the carrier.

Optionally, the pharmaceutical composition may also contain an antioxidant. The antioxidant is one known to those in the art, and can be e.g. butylated hydroanisole, butylated hydrotoluene, tocopherol and its derivative as α-Tocopherol polyethylene glycol succinate and mixtures thereof. It is generally present in an amount of from about 1% to about 10% by weight of the carrier.

One aspect of the current invention is the use of the composition according to the invention for the manufacture of a medicament for preventing or treating a parasite infestation of an animal.

By "treating" or "treat" or "treatment" is intended, the application or administration of a composition of the invention to an animal that has a parasitic infestation for the eradication of the parasite or the reduction of the number of the parasites infesting such animal.

The effect of the composition according to this invention can be e.g. ovicidal, larvicidal and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate.

"Prophylaxis" or "prevention" means that a new infestation of the animal with parasites is prevented by killing adult parasites and any development/larval stage, that is able to infest the host, before infestation of the host or directly after infestation of the protected host or by preventing generation of offspring of the parasites e.g. reducing the number of eggs laid and/or the hatching rate.

An "effective amount," is the amount or quantity of an isoxazoline compound that is required to alleviate or reduce parasite numbers on an animal and/or in an animal's environment e.g. the house/building, and/or to inhibit the development of parasite infections in an animal, in whole or in part.

This amount is readily determined by observation or detection of the parasite numbers either on the animal on in an animal's environment (e.g. by a trap) both before and after administering an isoxazoline compound via drinking water to such animals e.g. the parasite count is reduced, after a first administration, by 5% to 100%.

Hence, one aspect of the current invention is the pharmaceutical composition according to the invention comprising such composition for use in the prevention or treatment of parasite infestations. Such parasite infestations can be either infestations by ectoparasites or endoparasites.

In one embodiment the parasite infestation that is prevented or treated is an ectoparasite infestation. Specific examples of ectoparasites include, but are not limited to, fleas (*Ctenocephalides fells, Ctenocephalides* sp. and the like), ticks (*Rhipicephalus* sp., *Ixodes* sp., *Dermacentor* sp., *Amblyomma* sp., *Haemaphysalis* sp., *Boophilus* sp. and the like), and mites (*Demodex* sp., *Sarcoptes* sp., *Otodectes* sp., *Cheyletiella* sp., *Dermanyssus* sp, *Ornithonyssus* spp. and the like), lice (*Trichodectes* sp., *Felicola* sp., *Linognathus* sp., and the like), mosquitoes (*Aedes* sp., *Culex* sp., *Anoph-*

*eles* sp., and the like) and flies (*Hematobia* sp. including *Haematobia irritans, Musca* sp., *Stomoxys* sp. including *Stomoxys calcitrans, Dermatobia* sp., *Cochliomyia* sp., and the like).

In general the composition according to the current invention can be administered to all species of animals that need treatment or prevention of parasitic infections such as pigs, cattle, horse, goat, sheep, cat, dog, poultry and fish.

In one embodiment the animal is a livestock animal such as pigs, cattle, goat, sheep or poultry.

In another embodiment the animal is a companion animal such as dog, cat or horse. In another embodiment the animal is poultry or pig.

The composition according to the invention is preferably administered by systemic administration routes. "Systemic administration" is an administration at a site remote from a site wherein at least a portion of the target parasites reside.

With systemic administration, at least a portion of the compound reaches the target parasite via the animal recipient's bloodstream, other body fluids (lymph fluids), and/or tissues (e.g., skin or fat tissue).

Typically, the parasite ingests the compound along with the animal recipient's blood, other body fluids, and/or tissue.

Systemic administration may be achieved in several forms, e.g. oral, parenteral or topical.

The pharmaceutical composition may be administered parenterally, such as via intramuscular injection, intravenous injection, or subcutaneous injection.

Alternatively (or additionally) the composition according to the invention may be systemically administered topically using a transdermal formulation (i.e., a formulation that passes through the skin).

Such transdermal formulation can be e.g. in the form of a dip, spot-on, a pour-on, or a spray. Especially in case of a spray formulation the pharmaceutical composition can be diluted with water to form a spray formulation.

Alternatively the pharmaceutical composition can be administered as a bath or dip, e.g. for sheep or cattle. In order to prepare such a dip or bath formulation the pharmaceutical composition is diluted with water.

The pharmaceutical composition according to the invention can be diluted directly with water, or a pre-diluted (micellar) solution, as described below is diluted with a defined volume of water until an effective (amount) concentration of the isoxazoline compound in the water or the desired administration route is achieved.

A pre-diluted (micellar) solution can be prepared from the pharmaceutical composition as described above (concentrated solution) by mixing with a defined volume of water. Such a pre-diluted solution can be further diluted in 1 to 5 steps. Such pre-diluted solution comprises 1 to 85% v/v of water, especially 1, 5, 10, 20, 30, 40, 50, 55, 60, 65, 70, 75, 80 or 85%. Such solution can be administered to animals in the form of medicated drinking water.

In some embodiments, the composition according to the invention is systemically administered via an oral route in a unit dosage form, such as, for example, a solution, a suspension (aqueous or non-aqueous), an emulsion (oil-in-water or water-in-oil), an elixir, a syrup, or a drench.

One preferred administration form of an oral unit dosage form is a drench that is e.g. administered with the help of a "drenching gun" through the animals mouth especially to ruminant animals, e.g. sheep, goat or cattle, especially sheep.

Alternatively oral administration can be performed via the animal recipient's feed or drinking water e.g. for feed, it may be intimately dispersed in the animal recipient's regular feed, used as a top dressing, or liquid that is added to the finished feed.

In one preferred embodiment the composition is orally administered via the drinking water. Hence, this invention also is directed to the pharmaceutical composition as described in this specification for use in the prevention or treatment of parasitic arthropod infestations of animals.

It has been shown in the examples (see Example 5) that the pharmaceutical composition can be used to effectively control parasitic arthropod infestations of animals.

Example 5 shows that a the drinking water administration to poultry animals of pharmaceutical composition according to the current invention comprising an isoxazoline compound as described in this specification, in this case fluralaner, resulted 99% inhibition of red poultry mites for at least 15 days. By such inhibition of parasites the lifecycle of such parasitic arthropods can be interrupted and the establishing of a new significant population in the production unit can be prevented for the whole production cycle.

In one embodiment such animals such animals are laying hens that are producing eggs for human consumption. Such a pharmaceutical composition is also referred to as "concentrated pharmaceutical composition" or either as "concentrated solution".

Such pharmaceutical composition may be manufactured by processes known in the art. These processes include, for example, a variety of known mixing, dissolving, and emulsifying processes.

Preferably, the pharmaceutical composition is intended to be used to prepare medicated drinking water for administering the medicament to the animal via the animal's drinking water.

Therefore, another embodiment of the invention provides medicated drinking water comprising a mixture of a pharmaceutical composition as disclosed above and water.

Medicated drinking water is generally drinking water that contains a pharmaceutically active ingredient and water.

Medicated drinking water is produced by mixing and diluting the amount (volume) of the pharmaceutical composition as described above with water until the concentration of the isoxazoline compound that provides an effective amount of the isoxazoline compound for the number of animals treated with a volume of drinking water that corresponds to the volume that will be consumed during the treatment period to a large extend by the animals.

A pre-diluted (micellar) solution that can be used in the preparation of medicated drinking water as described above, can be prepared from the pharmaceutical composition as described above (concentrated solution) by mixing with an defined volume of drinking water.

Such a pre-diluted solution can be further diluted in 1 to 5 steps to manufacture medicated drinking water. Such pre-diluted solution comprises 1 to 85% v/v of water, especially 1, 5, 10, 20, 30, 40, 50, 55, 60, 65, 70, 75, 80 or 85%.

One aspect of the current invention is a method for preparing medicated drinking water wherein the pharmaceutical composition is diluted by injecting through a dosing pump system in a water system or by mixing with water in a medication tank.

Through medicated drinking water the pharmaceutical composition as described above can be delivered to the target animal through a drinking water system of choice by means of mixing and diluting the composition with drinking water in the central water tank or separate medication and storage tank.

Alternatively medicated drinking water can be prepared by injecting the composition according to the invention continuously into a high or low pressure ring system for drinking water distribution, using a dosage dispenser or dosing pump system or proportioner medication system.

Dosing pump systems rely on a pump that delivers measured amounts of a concentrate into the water pipes at a typical dilution of 1-5%.

Within the dosing pump systems, electronic dosing pump systems such as KONTI-DOS from Buerkert or mechanical dosing pump such as DOSATRON® water powered dosing pump, DOSMATIC® water-driven, proportional medicators can be used. The variety of field installations also concerns the water supply systems themselves: dead end or closed loop systems in different lengths with different pipe materials (e.g. PVC, galvanized iron) and the drinkers which are adapted to the target animals such as bell drinkers, nipples.

In one embodiment the pharmaceutical composition can be used to treat or prevent parasite infestations of animals, especially livestock animals (e.g., cattle, poultry and pigs) with isoxazoline compounds e.g. fluralaner, via drinking water systems.

The final isoxazoline compound concentration in the medicated drinking water is depending on the effective amount, the animal body weight, the animal water consumption and the treatment period.

In general the effective amount per kg body weight of the animals treated is dictated by the parasitic species infection being treated and is known in the art.

The medicator uses for example 10 ml of the pharmaceutical composition as defined above (concentrated solution) and further dilutes with water in about a 1:200 ratio to obtain medicated drinking water having an isoxazoline compound e.g. fluralaner, concentration of 0.001 to about 1 mg/ml, especially from about 0.05 to about 0.5 mg/ml.

In one embodiment the medicated water has a concentration of between 0.002 and 0.2 mg/ml of the isoxazoline compound.

In one specific embodiment for the specific isoxazoline compound fluralaner, the concentration in the medicated drinking water is calculated to provide the targeted amount of fluralaner per body weight (BW) of the poultry being treated in the range of from about 0.1 mg to about 2 mg of fluralaner per kilogram of body weight per day.

Such amount is present in the volume of drinking water normally consumed by the poultry being treated in a 2 to 24 hour treatment period, preferably 4-5 to 8 hours.

The pharmaceutical composition can be made available during the treatment period to a single animal; or at the same time to a group of animals or to all animals in a single stable (house) or farm via medicated drinking water.

The administration of the pharmaceutical composition through medicated drinking water as defined earlier is especially useful for poultry and pigs. In case of poultry it is especially useful for chickens and turkey.

The administration of the pharmaceutical composition via medicated drinking water as defined earlier is especially useful in types of fowl animals that are kept on a commercial scale, such as, laying hens, rearing pullets or replacement chickens, layer breeders, broiler chicken, and broiler rearing pullets and breeders.

However, the administration of the pharmaceutical composition via medicated drinking water as defined earlier can be also used in other types of poultry, such as e.g. turkey, geese, ducks, pigeons, quails or pheasants.

The administration to poultry animals that are kept for breeding or egg laying that are kept longer than approximately 8 weeks is preferred. This includes such poultry animals that currently do not (yet) lay eggs (such as e.g. replacement chickens). Especially preferred is the administration to laying hens.

The term "Laying hen" or "layer" is a common term for adult female, chickens (common domestic fowl (Gallus domesticus), that are primarily kept for laying eggs. Such eggs are generally used for consumption as human food.

The treatment frequency with the pharmaceutical composition via medicated drinking water is depending on the parasite treated or prevented (and its biological lifecycle) and the production cycle of the host animal treated.

The pharmaceutical composition according to the current invention is administered via medicated drinking water at least once, or twice per production cycle of the host animal treated (e.g. laying period in case of laying hens).

By this administration of the pharmaceutical composition via medicated water a higher efficacy against the parasites can be achieved, because of the different lifecycle stages of the parasites that can be reached. By such administration regimen the parasite population can be reduced to a level that only causes minimal damage to the animal and minimal production losses.

For some parasites, not all stages of the parasites can be reached by a single administration of the pharmaceutical composition via medicated drinking water because specific parasite stages either do not feed on the animal, or are not sufficiently controlled by the administration of the pharmaceutical composition via medicated drinking water.

With the administration of a second dose of the pharmaceutical composition via medicated drinking water the parasites can be reached, that developed (following the lifecycle of the parasites) from not susceptible, or difficult to reach parasite stages, e.g. that matured from the juvenile stages of the parasites (such as eggs, nymphs or pupae) during this period.

Especially preferred is the administration of the pharmaceutical composition via medicated drinking water approximately 7 days or 14 days apart (depending on the parasite lifecycle and production cycle of the host animal) once or twice during a production cycle. Especially preferred is the administration 7 days apart.

In one embodiment the pharmaceutical composition via medicated drinking water is administered to treat or prevent a mite infestation. Certain mites migrate from birds, rodents, food material, vegetable matter and house dust and can attack and annoy animals and humans. There are different categories of mites including Northern fowl mites (*Ornithonyssus sylviarum*), chicken red mites (*Dermanyssus gallinae*, follicle mites (*Demodex folliculorum*), itch or scabies mites (*Sarcoptes* spp., *Cheyletiella* spp., *Psorioptes* spp.).

In a preferred embodiment the mite infestation is a mite infestation of poultry, especially of *Dermanyssus* sp. (e.g. *D. gallinae*) and/or *Ornithonyssus* sp., especially *Ornithonyssus sylviarum*.

In one embodiment the administration of the pharmaceutical composition via medicated drinking water according to the invention controls the stages of parasitic arthropods, as described above that are present in the environment of poultry animals. The parasitic arthropod stages can be all stages of the lifecycle that are known to the skilled person, i.e. both juvenile stages (development/larval) and adult stages.

In one embodiment the administration of the pharmaceutical composition via medicated drinking water according to the invention controls arthropods in the environment of poultry animals, and especially broiler chickens that generally do not infest animals directly, but provide harm to the animals, such as e.g. darkling beetles.

EXAMPLES

Example 1

Preparation of Concentrated Solution

The compositions were prepared according to the following procedure:

The required quantity of surfactant and solvent was weight in adapted containers and the excipients in were poured the manufacturing vessel and weighed back to introduce the required quantities. The mixture was stirred until complete homogenization. The active ingredient (isoxazoline compound) was added to the surfactant/solvent mixture under deflocculated paddle stirring and the mixture was stirred under deflocculated paddle stirring until complete dissolution of the active ingredient With this method the following compositions (concentrated solutions) comprising 1% w/w of Fluralaner was prepared:

| Component | Composition (% w/w) |
|---|---|
| Transcutol V | 25% |
| Tween 80 | 75% |

| Component | Composition (% w/w) |
|---|---|
| Ethyl lactate | 12.5% |
| Transcutol HP | 12.5% |
| Tween 80 | 75% |

| Component | Composition (% w/w) |
|---|---|
| Ethyl lactate | 25% |
| Transcutol HP | 25% |
| Tween 80 | 50% |

| Component | Composition (% w/w) |
|---|---|
| Ethyl lactate | 37.5% |
| Transcutol HP | 37.5% |
| Tween 80 | 25% |

| Component | Composition (% w/w) |
|---|---|
| Soluphor P | 12.5% |
| Transcutol HP | 12.5% |
| Tween 80 | 75% |

| Component | Composition (% w/w) |
|---|---|
| Soluphor P | 25% |
| Transcutol HP | 25% |
| Tween 80 | 50% |

The stability of the concentrated solution in 10 ml glass vials was investigated at 25° C./60% RH and 40° C./75% RH during 12 months. The solution was stable at least 12 months at 25° C./60% RH and 40° C./75% RH.

Example 2

Preparation of Pre-Diluted (Micellar) Solution

Pre-diluted solutions were prepared by preparing of a solution of 10% w/w fluralaner in either transcutol V or mixture transcutol V/ethyl lactate in a 10 ml glass vial and adding the surfactant and shaking. Thereafter purified water was added to solvent/surfactant mixture and shaked.

The stability of diluted fluralaner solution at 1 µg/ml (Tween 80/Transcutol V 75/25 10 ml-glass vial was investigated. The solutions was stable for 2 days at 25° C./60% RH and at least 15 days at 2-8° C.

The following pre-diluted solutions were prepared and the solution stability (forming of precipitation) tested. Pre-diluted solutions were observed at t=0 and one aliquot was stored in refrigerator at 2-8° C. and one at 40° C./75% RH for 28 days. Stability of the solution (precipitation) was assessed visually on days D0, D1, D2, D5, D7, D14, D21 and D28.

The evaluated compositions are shown in Table 1 below: TRV=Transcutol V, EL=Ethyl lactate

| Fluralaner concentration mg/g | Solvent TRV = Transcutol V, EL = Ethyl lactate | Surfactant | Water |
|---|---|---|---|
| 99 | 10% EL/TRV | 89% Tween 80 | 1% |
| 99 | 10% TRV | 89% Tween 80 | 1% |
| 95 | 10% EL/TRV | 85% Tween 80 | 5% |
| 95 | 10% TRV | 85% Tween 80 | 5% |
| 90 | 10% EL/TRV | 80% Tween 80 | 10% |
| 90 | 10% TRV | 80% Tween 80 | 10% |
| 80 | 10% EL/TRV | 70% Tween 80 | 20% |
| 80 | 10% TRV | 70% Tween 80 | 20% |
| 70 | 10% EL/TRV | 60% Tween 80 | 30% |
| 70 | 10% TRV | 60% Tween 80 | 30% |
| 60 | 10% EL/TRV | 50% Tween 80 | 40% |
| 60 | 10% TRV | 50% Tween 80 | 40% |
| 50 | 10% EL/TRV | 40% Tween 80 | 50% |
| 50 | 10% TRV | 40% Tween 80 | 50% |
| 45 | 10% EL/TRV | 35% Tween 80 | 55% |
| 45 | 10% TRV | 35% Tween 80 | 55% |
| 45 | 20% EL/TRV | 70% Tween 80 | 10% |
| 40 | 10% EL/TRV | 30% Tween 80 | 60% |
| 40 | 10% TRV | 30% Tween 80 | 60% |
| 40 | 20% EL/TRV | 60% Tween 80 | 20% |
| 40 | 20% TRV | 60% Tween 80 | 20% |
| 35 | 10% TRV | 25% Tween 80 | 65% |
| 35 | 10% EL/TRV | 25% Tween 80 | 65% |
| 35 | 20% EL/TRV | 50% Tween 80 | 30% |
| 35 | 20% TRV | 50% Tween 80 | 30% |
| 30 | 10% EL/TRV | 20% Tween 80 | 70% |
| 30 | 10% TRV | 20% Tween 80 | 70% |
| 30 | 20% EL/TRV | 40% Tween 80 | 40% |
| 30 | 20% TRV | 40% Tween 80 | 40% |
| 30 | 30% EL/TRV | 60% Tween 80 | 10% |
| 30 | 30% TRV | 60% Tween 80 | 10% |
| 25 | 10% EL/TRV | 15% Tween 80 | 75% |
| 25 | 10% TRV | 15% Tween 80 | 75% |
| 25 | 20% EL/TRV | 30% Tween 80 | 50% |
| 25 | 20%/TRV | 30% Tween 80 | 50% |
| 25 | 30% EL/TRV | 45% Tween 80 | 25% |
| 25 | 30% TRV | 45% Tween 80 | 25% |
| 20 | 10% TRV | 10% Tween 80 | 80% |
| 20 | 10% EL/TRV | 10% Tween 80 | 80% |
| 20 | 20% EL/TRV | 20% Tween 80 | 60% |
| 20 | 20% TRV | 20% Tween 80 | 60% |
| 20 | 30% EL/TRV | 30% Tween 80 | 40% |
| 20 | 30% TRV | 30% Tween 80 | 40% |
| 20 | 40% EL/TRV | 40% Tween 80 | 20% |
| 20 | 40% TRV | 40% Tween 80 | 20% |
| 15 | 10% TRV | 5% Tween 80 | 85% |

-continued

| Fluralaner concentration mg/g | Solvent TRV = Transcutol V, EL = Ethyl lactate | Surfactant | Water |
|---|---|---|---|
| 15 | 10% EL/TRV | 5% Tween 80 | 85% |
| 15 | 20% EL/TRV | 10% Tween 80 | 70% |
| 15 | 20% TRV | 10% Tween 80 | 70% |
| 15 | 30% EL/TRV | 15% Tween 80 | 55% |
| 15 | 30% TRV | 15% Tween 80 | 55% |
| 15 | 40% EL/TRV | 20% Tween 80 | 40% |
| 15 | 40% TRV | 20% Tween 80 | 40% |
| 15 | 50% EL/TRV | 25% Tween 80 | 25% |
| 15 | 50% TRV | 25% Tween 80 | 25% |

Results:

Stability study of diluted solutions of fluralaner in ethyl lactate/Transcutol V/Tween 80/purified water: No precipitate of fluralaner was observed with diluted solutions in 5 days following dilution except for diluted solution EL/TRV-TW80'-W-40-20-40 which was precipitated on Day 5., but not during the any other observations dung the 28 day period.

Stability study of diluted solutions Transcutol V/Tween 80/Purified Water: Only one diluted solution, TRV-TW80-W-10-5-85 formed precipitates on Day 5 at 2-8° C. and 40° C./75% RH.

Example 3

Stability of Medicated Drinking Water

Stability of diluted Fluralaner solution at 1 µg/ml, 2 µg/ml, 10 µg/ml and 20 µg/ml (Tween 80/Transcutol V 75/25 in 25 m-pipes (PE material) was evaluated. The solutions were stable during 4 hours (treatment simulation).

Example 4

Technological Study

The study was conducted in a commercial poultry house for approximately 36000 replacement chickens with 4 batteries each with 3 levels. 4 PVC water dead-end pipes, (78 m long) supplied water for each battery.

Drinking nipples (Big Dutchman types "screw nipples" and "Top", equipped with a single-arm plastic drip cup) were fitted to the water pipes. In this facility the delivery of the concentrated composition to the drinking nipples using both a dosing pump system and a medication tank was evaluated.

a) Dosing Pump

The dosing pump and its stock solution container were installed in a water hose coming from the water supply pipe and ending in a water tank that was metered for 105 L.

The dosing pump was set for 5% injection rate. The stock solution container was filled with a total of 8.8 L (175×0.05 [5%]).

Once the container was filled, the calculated volume of 193 mL of the concentrated composition was poured into the container and subsequently stirred.

The dosing pump was connected to the water distribution pipe and the pipe system filled with the medicated water.

b) Medication Tank

The medication tank was filled with 175 L of tap water.

The calculated volume of 193 mL of the concentrated composition was poured into the container and subsequently stirred.

The medication tank was connected to the water distribution pipe and the pipe system filled with the medicated water.

No animals were present in the cages. Therefore the water lines were opened every 10 min to mimic a continuous (intermittent) drinking water flow. At each draining 7.3 L of medicated water was allowed to drain at the dead-end side of the pipe.

Samples of medicated water was taken from 6 drinking nipples: the first and last drinking nipple in a drinker line, and from 4 drinking nipples having an equal distance at pre-defined time points, with a maximum of 4 h and analysed for fluralaner concentration.

Results:

TABLE 2

Medication tank system Fluralaner concentration in drinking nipples - Percent of nominal concentration: 11.0 µg/mL = 100%

|  | T 30 min | T 60 min | T 120 min | T 180 min | T 240 min |
|---|---|---|---|---|---|
| Nipple 1 | −5 | −4 | −4 | −5 | −10 |
| Nipple 2 | −7 | −5 | −4 | −5 | −4 |
| Nipple 3 | −5 | −4 | −4 | −4 | −4 |
| Nipple 4 | −6 | −5 | −4 | −4 | −3 |
| Nipple 5 | −8 | −4 | −4 | −4 | −6 |
| Nipple 6 | −6 | −6 | −4 | −5 | −4 |

TABLE 3

Dosing pump system Fluralaner concentration in drinking nipples - Percent of nominal concentration: 9.7 µg/mL = 100%

|  | T 30 min | T 60 min | T 120 min | T 180 min | T 240 min |
|---|---|---|---|---|---|
| Nipple 1 | −10 | −10 | −9 | −9 | −9 |
| Nipple 2 | −9 | −14 | −12 | −9 | −9 |
| Nipple 3 | −9 | −10 | −10 | −14 | −14 |
| Nipple 4 | −12 | −16 | −14 | −10 | −10 |
| Nipple 5 | −12 | −10 | −11 | −10 | −10 |
| Nipple 6 | −26 | −10 | −11 | −11 | −10 |

The fluralaner concentration in the drinking water remains constant over time and along the drinking water line as a deviation around 20% is generally acceptable in this form of administration (up to 4 hours).

Example 5

Efficacy Study

The efficacy of fluralaner administered orally via medicated drinking water, to control artificially induced poultry red mite infestations (*Dermanyssus gallinae*) of laying hens was investigated. Groups A-D (n=6) were treated with doses of 2, 1 and 0.5 mg fluralaner/kg BW once or 1 mg fluralaner/kg BW twice (0.5 mg/kg BW on 2 occasions).

Materials and Methods:

Drinking water consumption in each was measured on three days prior to administration to calculate the average daily water consumption. Medicated water was prepared by diluting a fluralaner solution (10 mg/mL) as shown in the table below to the calculated fluralaner concentration.

| Components | Composition (% w/w) | Composition (mg/mL) | Function |
|---|---|---|---|
| Fluralaner | 0.95% | 10 | Active ingredient |
| Transcutol V (diethylene glycol monoethyl ether) | 24.76% | Up to 1 mL* | Solvent |
| Tween 80 | 74.29% | | Surfactant |

On D0 (group D additionally on D7), the hens in groups A-D received fluralaner via medicated drinking water. Group E received un-medicated drinking water ad libitum.

The dose to be administered was calculated based on average body weights of each treatment group, obtained one day before treatment (D-1, D 6). A fluralaner stock solution was diluted in the drinking water to prepare medicated water ready for consumption.

Medicated drinking water was prepared so that fluralaner was administered according to the following dosing regimen:

The volume of medicated water offered per group on D0 (group D also on D7) was approximately 50% of the calculated mean daily water intake measured previously in the respective group in order to ensure consumption of the full dose.

Once all medicated water was consumed the other 50% volume of the mean daily water intake was supplied as tap water in the same drinker.

On Day 1, Day 5, Day 8, Day 12, D15, D19 and D22 four of six hens per group were infested with approximately 200 vital, *D. gallinae* mites (unfed nymphs and adults that starved before infestation for 7 days).

From each infested hen approximately 25 engorged mites were collected and incubated for approximately 24 hours. The dead, damaged and/or live mites were counted visually using a binocular.

Mites were classified as dead if no movement was determined or mites lay in a dorsal position. Mites were classified as damaged if their movement was uncoordinated.

The Mite Mortality and Mite Inhibition percentage was calculated for each treated group in comparison to a not-treated negative control group.

Results:

Fluralaner was well tolerated in hens.

The % Mortality and % Inhibition of red mites (*Dermanyssus gallinae*) assessed approximately 24 hours after the infestation of hens that received fluralaner orally via drinking water are given in Tables 1 and 2. A fast onset of action was demonstrated for all administered doses.

TABLE 1

% Mortality of *D. gallinae* assessed 24 hours after infestation

| Group | fluralaner (mg/kg BW) | % Mortality of mites 24 hours after infestation on | | | | | | |
|---|---|---|---|---|---|---|---|---|
| | | D1 | D5 | D8 | D12 | D15 | D19 | D22 |
| A | 2 | 100 | 100 | 100 | 100 | 77 | 1 | 0 |
| B | 1 | 100 | 100 | 100 | 94 | 77 | 2 | 0 |
| C | 0.5 | 100 | 100 | 97 | 55 | 15 | 0 | 0 |
| D | 1 (2 × 0.5) | 100 | 100 | 100 | 100 | 98 | 59 | 14 |

TABLE 2

% Inhibition of *D. gallinae* assessed 24 hours after infestation

| Group | fluralaner (mg/kg BW) | % Mortality of mites 24 hours after infestation on | | | | | | |
|---|---|---|---|---|---|---|---|---|
| | | D1 | D5 | D8 | D12 | D15 | D19 | D22 |
| A | 2 | 100 | 100 | 100 | 100 | 81 | 14 | 0 |
| B | 1 | 100 | 100 | 100 | 95 | 81 | 3 | 0 |
| C | 0.5 | 100 | 100 | 100 | 75 | 19 | 0 | 0 |
| D | 1 (2 × 0.5) | 100 | 100 | 100 | 100 | 99 | 66 | 27 |

On each assessment time points, mites observed from the untreated control group were vital and showed their normal behavior.

The invention claimed is:

1. A method of preventing or treating parasite infestations in animals by administering to such animal in its drinking water a pharmaceutical composition consisting essentially of fluralaner or a salt or solvate thereof, and a pharmaceutically acceptable carrier consisting essentially of ethyl lactate, diethylene glycol monoethyl ether and a polysorbate surfactant.

2. The method according to claim 1 wherein the amount of fluralaner is between 1.5 mg/ml and 100 mg/ml.

3. The method according to claim 1 wherein the ratio of diethylene glycol monoethyl ether to polysorbate surfactant is <50:50% w/w.

4. The method according to claim 1 wherein the animals are selected from pigs and poultry.

5. The method according to claim 4 wherein the animals are laying hens.

6. The method according to claim 1 wherein the parasite infestation is a mite infestation.

7. The method according to claim 6 wherein the mite infestation is an infestation with *Dermanyssus* sp. or *Ornithonyssus* sp.

8. A medicated drinking water consisting essentially of a mixture of a pharmaceutical composition consisting essentially of fluralaner or a salt or solvate thereof, and a pharmaceutically acceptable carrier consisting essentially of ethyl lactate, diethylene glycol monoethyl ether and a polysorbate surfactant and water.

9. The medicated drinking water according to claim 8 wherein the amount of fluralaner or a salt or solvate thereof is between 0.001 and 100 mg/ml.

10. A Method for preparing medicated drinking water according to claim 8 wherein the pharmaceutical composition is diluted by injecting through a dosing pump system in a water system or by mixing with water in a medication tank.

11. The medicated drinking water of claim 8, wherein the ratio of diethylene glycol monoethyl ether to polysorbate surfactant is <50:50% w/w.

* * * * *